United States Patent
Nguyen et al.

(10) Patent No.: US 9,839,468 B2
(45) Date of Patent: Dec. 12, 2017

(54) ELECTROSURGICAL DEVICE WITH INTERNAL DIGESTOR ELECTRODE

(71) Applicant: AnthroCare Corporation, Austin, TX (US)

(72) Inventors: Kim Nguyen, Austin, TX (US); Doug Evans, Austin, TX (US); Seth M. Pransky, La Jolla, CA (US)

(73) Assignee: ArthroCare Corporation, Austin, TX (US)

( * ) Notice: Subject to any disclaimer, the term of this patent is extended or adjusted under 35 U.S.C. 154(b) by 27 days.

(21) Appl. No.: 14/668,497

(22) Filed: Mar. 25, 2015

(65) Prior Publication Data

US 2015/0196346 A1    Jul. 16, 2015

Related U.S. Application Data

(62) Division of application No. 13/409,762, filed on Mar. 1, 2012, now Pat. No. 9,011,428.

(60) Provisional application No. 61/448,289, filed on Mar. 2, 2011.

(51) Int. Cl.
| | |
|---|---|
| *A61B 18/14* | (2006.01) |
| *A61B 18/04* | (2006.01) |
| *A61B 18/16* | (2006.01) |
| *A61B 18/00* | (2006.01) |

(52) U.S. Cl.
CPC ........ *A61B 18/042* (2013.01); *A61B 18/1402* (2013.01); *A61B 2018/00583* (2013.01); *A61B 2018/144* (2013.01); *A61B 2018/1472* (2013.01); *A61B 2018/162* (2013.01); *A61B 2218/002* (2013.01); *A61B 2218/005* (2013.01); *A61B 2218/007* (2013.01)

(58) Field of Classification Search
CPC ................ A61B 18/14; A61B 18/1492; A61B 2018/002; A61B 2018/00577; A61B 2218/007
USPC ......................................... 607/32, 41, 45, 46
See application file for complete search history.

(56) References Cited

U.S. PATENT DOCUMENTS

| | | | | |
|---|---|---|---|---|
| 6,565,561 | B1 * | 5/2003 | Goble | A61B 18/1485 606/41 |
| 2003/0097129 | A1 * | 5/2003 | Davison | A61B 18/14 606/41 |
| 2003/0216725 | A1 * | 11/2003 | Woloszko | A61B 18/1402 606/41 |
| 2003/0225403 | A1 * | 12/2003 | Woloszko | A61B 18/148 606/41 |
| 2004/0006339 | A1 * | 1/2004 | Underwood | A61B 18/148 606/45 |
| 2008/0234673 | A1 * | 9/2008 | Marion | A61B 18/1482 606/45 |

(Continued)

*Primary Examiner* — Allen Porter, Jr.
(74) *Attorney, Agent, or Firm* — David A. Warmbold

(57) ABSTRACT

An electrosurgical wand is described, for treating a target tissue using electrosurgical energy, which has an elongate shaft with a handle end and a distal end. A first active electrode surface is disposed on the distal end of the shaft and a first digester electrode surface is recessed away from the first active electrode surface and electrically connected with the first active electrode surface. An aspiration aperture is also disposed adjacent the first active electrode surface and fluidly connected with an aspiration lumen, wherein the first digester electrode surface is disposed within the aspiration lumen.

19 Claims, 8 Drawing Sheets

(56) References Cited

U.S. PATENT DOCUMENTS

2012/0179157 A1* 7/2012 Frazier ............... A61B 18/148
  606/41

* cited by examiner

ELECTROSURGICAL DEVICE WITH INTERNAL DIGESTOR ELECTRODE

CROSS-REFERENCE TO RELATED APPLICATIONS

This application is a divisional of U.S. application Ser. No. 13/409,762 filed Mar. 1, 2012, which claims the benefit under 35 U.S.C. §119(e) of U.S. Provisional Application No. 61/448,289 filed Mar. 2, 2011, the complete disclosure of which is incorporated herein by reference for all purposes.

FIELD OF THE INVENTION

This invention relates generally to methods and apparatus for accessing and treating tissue, and more particularly to apparatus and methods for electrosurgically treating tissue such as laryngeal tissue.

BACKGROUND

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on a separate electrode for the return of current that is placed away from the surgical site on the body of the patient, and where the surgical device defines only a single electrode pole that provides the surgical effect. Bipolar devices comprise two or more electrodes on the same support for the application of current between their surfaces.

Electrosurgical procedures and techniques are particularly advantageous because they generally reduce patient bleeding and trauma associated with cutting operations. Additionally, electrosurgical ablation procedures, where tissue surfaces and volume may be reshaped, cannot be duplicated through other treatment modalities.

Radiofrequency (RF) energy is used in a wide range of surgical procedures because it provides efficient tissue resection and coagulation and relatively easy access to the target tissues through a portal or cannula. Conventional monopolar high frequency electrosurgical devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site. This collateral tissue damage often causes indiscriminate destruction of tissue, resulting in the loss of the proper function of the tissue. In addition, the device does not remove any tissue directly, but rather depends on destroying a zone of tissue and allowing the body to eventually remove the destroyed tissue.

Present electrosurgical devices used for tissue ablation in narrow anatomies may suffer from concerns associated with the difficulties that the device size may present in accessing certain treatment areas. Specifically, instances may arise where the device may have a shaft diameter that is too wide or shaft working length that is not sufficiently long making the desired access problematic. In additional, present devices used for tissue removal may suffer from poor visibility at the working end of the device where the overall size or orientation of the device tip obscures the physician's view of the surgical field. The inability to easily access and visualize the surgical field is a significant disadvantage in using electrosurgical techniques for tissue ablation, particularly in arthroscopic, otolaryngological, and spinal procedures.

Alternative devices for tissue treatment in narrow anatomies, such as $CO_2$ lasers or microdebriders, may suffer from additional shortcomings in addition to obstacles attributed to the size of the device. For example, a $CO_2$ laser may require a substantially longer set up time prior to the actual procedure, and such lasers are further impaired by relatively smaller tissue removal rate and increased collateral damage to tissue. Microdebriders typically are not afforded adequate hemostatis capabilities, resulting in the presence of significant amounts of blood likely contributing to blocked visibility of the surgical field and prolonged procedure times as other materials are required to stop bleeding.

Accordingly, improved systems and methods are still desired for precise tissue removal in narrow anatomies via electrosurgical ablation of tissue. In particular, improved systems operable designed to provide access to narrow anatomies while allowing increased surgical field visualization would provide a competitive advantage.

BRIEF DESCRIPTION OF THE DRAWINGS

For a detailed description of exemplary embodiments, reference will now be made to the accompanying drawings in which.

NOTATION AND NOMENCLATURE

Figure 1:
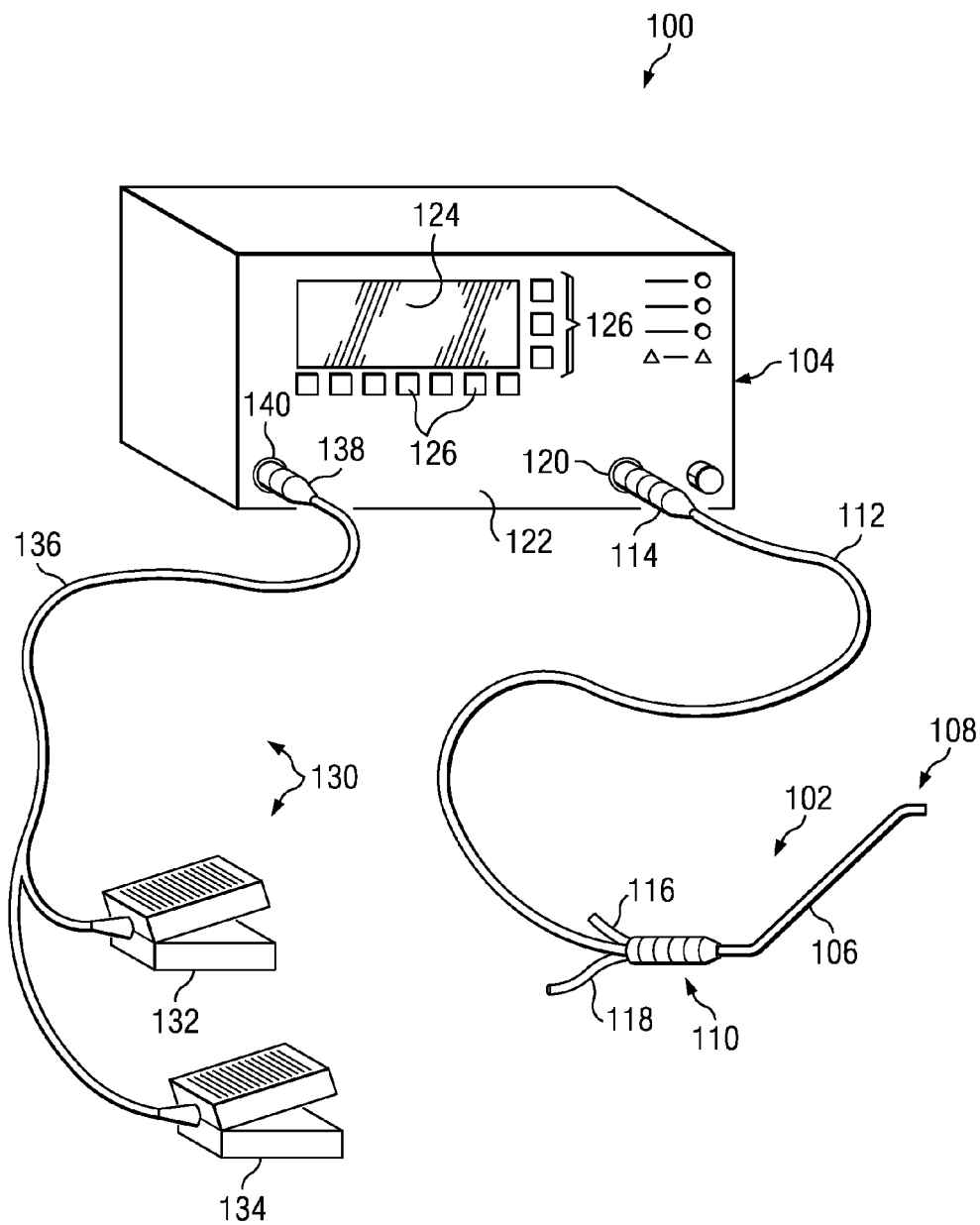
FIG. 1 shows an electrosurgical system in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect electrical connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow path for electrons with respect to an active electrode, and/or an electrode of an electrical surgical wand which does not itself produce an electrically-induced tissue-altering effect on tissue targeted for treatment.

"Digester electrode" or "digester surface" shall mean an electrode or a discrete, electrically connected portion of an active electrode of an electrosurgical wand which serves to produce an additional electrically-induced tissue-altering effect when brought into contact with, or close proximity to by-products or tissue remnants produced by the active electrode.

A fluid conduit said to be "within" an elongate shaft shall include not only a separate fluid conduit that physically resides within an internal volume of the elongate shaft, but also situations where the internal volume of the elongate shaft is itself the fluid conduit.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

FIG. 1 illustrates an electrosurgical system 100 in accordance with at least some embodiments. In particular, the electrosurgical system comprises an electrosurgical wand 102 (hereinafter "wand") coupled to an electrosurgical controller 104 (hereinafter "controller"). The wand 102 comprises an elongate shaft 106 that defines distal end 108 where at least some electrodes are disposed. The elongate shaft 106 further defines a handle or proximal end 110, where a physician grips the wand 102 during surgical procedures. The wand 102 further comprises a flexible multi-conductor cable 112 housing a plurality of electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a flexible tubular member 116 and a second flexible tubular member 118. In some embodiments, the flexible tubular member 116 is used to provide electrically conductive fluid (e.g., saline) to the distal end 108 of the wand. Likewise in some embodiments, flexible tubular member 118 is used to provide aspiration to the distal end 108 of the wand.

Still referring to FIG. 1, a display device or interface panel 124 is visible through the outer surface 122 of the controller 104, and in some embodiments a user may select operational modes of the controller 104 by way of the interface device 124 and related buttons 126.

In some embodiments the electrosurgical system 100 also comprises a foot pedal assembly 130. The foot pedal assembly 130 may comprise one or more pedal devices 132 and 134, a flexible multi-conductor cable 136 and a pedal connector 138. While only two pedal devices 132, 134 are shown, one or more pedal devices may be implemented. The outer surface 122 of the controller 104 may comprise a corresponding connector 140 that couples to the pedal connector 138. A physician may use the foot pedal assembly 130 to control various aspects of the controller 104, such as the operational mode. For example, a pedal device, such as pedal device 132, may be used for on-off control of the application of radio frequency (RF) energy to the wand 102, and more specifically for control of energy in an ablation mode. A second pedal device, such as pedal device 134, may be used to control and/or set the operational mode of the electrosurgical system. For example, actuation of pedal device 134 may switch between energy levels of an ablation mode.

The electrosurgical system 100 of the various embodiments may have a variety of operational modes. One such mode employs Coblation® technology. In particular, the assignee of the present disclosure is the owner of Coblation technology. Coblation technology involves the application of a radio frequency (RF) signal between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracellular or intracellular fluid. In other embodiments, the electrically conductive fluid may be a liquid or gas, such as isotonic saline. In some embodiments, such as surgical procedures on a disc between vertebrae, the electrically conductive fluid is delivered in the vicinity of the active electrode and/or to the target site by the wand 102, such as by way of the internal passage and flexible tubular member 116.

When the electrically conductive fluid is heated to the point that the atoms of the fluid vaporize faster than the atoms re-condense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm3 for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. Often, the electrons in the plasma carry the electrical current or absorb the electromagnetic waves and, therefore, are hotter than the ionic particles. Thus, the electrons, which are carried away from the target tissue toward the active or return electrodes, carry most of the plasma's heat, enabling the ionic particles to break apart the target tissue molecules in a substantially non-thermal manner.

By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882, the complete disclosure of which is incorporated herein by reference.

In addition to the Coblation mode, the electrosurgical system 100 of FIG. 1 may also in particular situations be useful for sealing larger arterial vessels (e.g., on the order of about 1 mm in diameter), when used in what is known as a coagulation mode. Thus, the system of FIG. 1 may have an ablation mode where RF energy at a first voltage is applied to one or more active electrodes sufficient to effect molecular dissociation or disintegration of the tissue, and the system of FIG. 1 may have a coagulation mode where RF energy at a second, lower voltage is applied to one or more active electrodes (either the same or different electrode(s) as the ablation mode) sufficient to heat, shrink, seal, fuse, and/or achieve homeostasis of severed vessels within the tissue.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Because different tissue structures have different molecular bonds, the electrosurgical system 100 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the Coblation® technology in some operational modes does not ablate such fatty tissue; however, the Coblation® technology at the lower energy levels may be used to effectively ablate cells to release the inner fat content in a liquid form. Other modes may have increased energy such that the double bonds can also be broken in a similar fashion as the single bonds (e.g., increasing voltage or changing the electrode configuration to increase the current density at the electrodes).

A more complete description of the various phenomena can be found in commonly assigned U.S. Pat. Nos. 6,355,032; 6,149,120 and 6,296,136, the complete disclosures of which are incorporated herein by reference.

Figure 2:
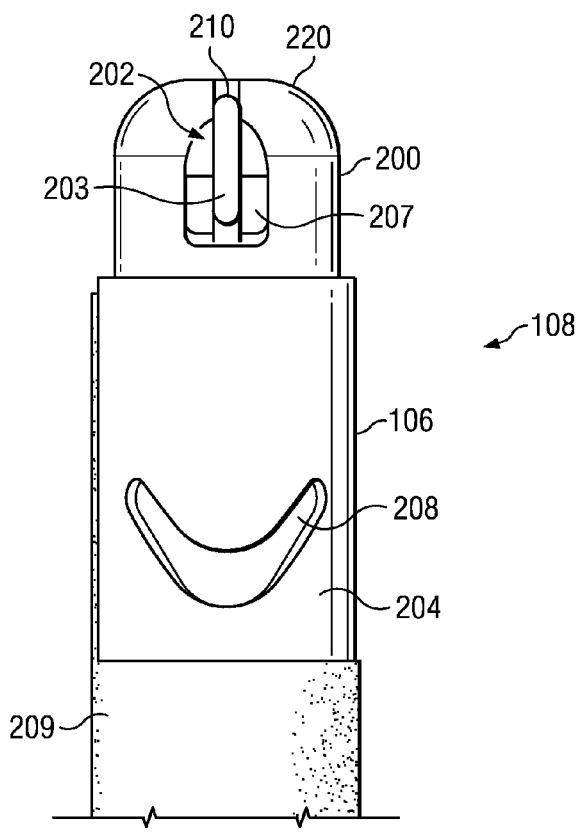
FIG. 2 shows an end elevation view of a wand in accordance with at least some embodiments.

FIG. 2 illustrates an end elevation view of the distal end 108 of wand 102 in accordance with at least some embodiments. In some embodiments, a portion of the elongate shaft 106 may be made of a metallic material (e.g., Grade TP304 stainless steel hypodermic tubing). In other embodiments, portions of the elongate shaft may be constructed of other suitable materials, such as inorganic insulating materials. The elongate shaft 106 may define a circular cross-section at the handle or proximal end 110 (not shown in FIG. 2), and at least a portion of the distal end 108 may also be circular in cross-section. For wands intended for use in otolaryngological procedures, and in particular for use in procedures where access to the larynx is desired, the diameter of shaft 106 may be 3 centimeters or less, and in some cases 2.8 millimeters. Additionally, the length of shaft 106 from handle 110 to the tip of distal end 108 may be 8.5 inches, and in some cases 7.5 inches. Other dimensions may be equivalently used when the surgical procedure allows.

In embodiments where the elongate shaft is metallic, the distal end 108 may further comprise a non-conductive spacer 200 coupled to the elongate shaft 106. In some cases the spacer 200 is ceramic, but other non-conductive materials resistant to degradation when exposed to plasma may be equivalently used (e.g., glass). The spacer 200 supports electrodes of conductive material, with illustrative active electrode labeled 202 in FIG. 2. Active electrode 202 defines an exposed surface area of conductive material, where active electrode 202 is a loop of wire of particular diameter. For embodiments using a loop of wire, the loop of wire may be molybdenum or tungsten having a diameter between and including 0.008 and 0.015 inches, and more preferably of 0.010 inches. In certain embodiments, the active electrode 202 has an exposed ablative surface 203 bridging aspiration aperture 207 wherein exposed surface 203 defines a straight portion of active electrode 202 that is oriented substantially parallel to the long axis of distal end 108.

In certain embodiments electrode 202 has an active electrode recessed secondary surface 210 that may be oriented substantially transverse to the long axis of the distal end 108 and may be recessed within the spacer 200, so that the surface 210 is disposed below a top surface 220 of the spacer 200. Secondary surface 210 may be recessed within an elongate nest provided by spacer 200, the nest being deep enough so that the secondary 210 may not treat tissue inadvertently, however is capable of applying energy to a target tissue, should the surgeon intentionally oppose this surface 210 against tissue so that the tissue extends into the recesses area around secondary electrode surface 210. Is alternative embodiments, this surface 210 may be insulated so as to not be an active surface (not shown here).

Referring still to FIG. 2, wand 102 includes a return electrode 204 for completing the current path between active electrode 202 and controller 104 (not shown in this figure). Return electrode 204 is suitably connected to controller 104. Return electrode 204 is preferably a semi-annular member defining the exterior of shaft 106, and a distal portion of return electrode 204 on the side of shaft 106 corresponding to the exposed surface 203 of active electrode 202 is preferably exposed (e.g., approximately half the circumference of return electrode 204 is exposed and free of insulative covering). Additionally, a section of the distal portion of return electrode 204 may be disposed within sheath 209, preferably the section disposed on the opposite side of shaft 106 from exposed surface 203 of active electrode 202. At least a proximal portion of return electrode 204 is disposed within an electrically insulative sheath 209, which is typically formed as one, or more electrically insulative sheaths or coatings, such as polytetrafluoroethylene, polyimide, and the like. The provision of the electrically insulative sheath 209 encircling over a portion of return electrode 204 may minimize prevents direct electrical contact between return electrode 204 and any adjacent body structure or the surgeon. Such direct electrical contact between a body structure (e.g., tendon) and an exposed common electrode member 204 could result in unwanted heating and necrosis of the structure at the point of contact causing necrosis. Return electrode 204 is preferably formed from an electrically conductive material, usually metal, which is selected from the group consisting of stainless steel alloys, platinum or its alloys, titanium or its alloys, molybdenum or its alloys, and nickel or its alloys.

In some embodiments saline is delivered to the distal end 108 of wand, possibly to aid in plasma creation. Referring still to FIG. 2, discharge aperture 208 is illustrated on the distal end 108 disposed through return electrode 204. Discharge aperture 208 is formed through the exposed portion of return electrode 204 on the same side of shaft 106 as exposed surface 203 of active electrode 202. It is preferable that discharge aperture 208 is disposed proximally of aspiration aperture 207 and the exposed surface 203 of active electrode 202. The discharge aperture 208 is fluidly coupled to the flexible tubular member 116 (FIG. 1) by way of a fluid conduit within the wand 102. Thus, saline or other fluid may be pumped into the flexible tubular member 116 (FIG. 1) and discharged through discharge aperture 208 to further aid in developing consistent wetting around the exposed surface or circumference of return electrode 204. Discharge aperture 208 is disposed towards the proximal end of return electrode 204, so that a large portion of the return electrode surface area is sufficiently wetted, as the fluid travels from the discharge aperture 208 towards the exposed surface 203. Discharge aperture 208 is approximately crescent or boomerang shaped with the widest portion or widest opening, as measured parallel to distal end long axis, substantially in line with active surface 203. This aperture 208 shape has been found to produce a preferable uniform and directed flow, distally, over the return electrode surface and towards the active electrode 202.

Figure 3:
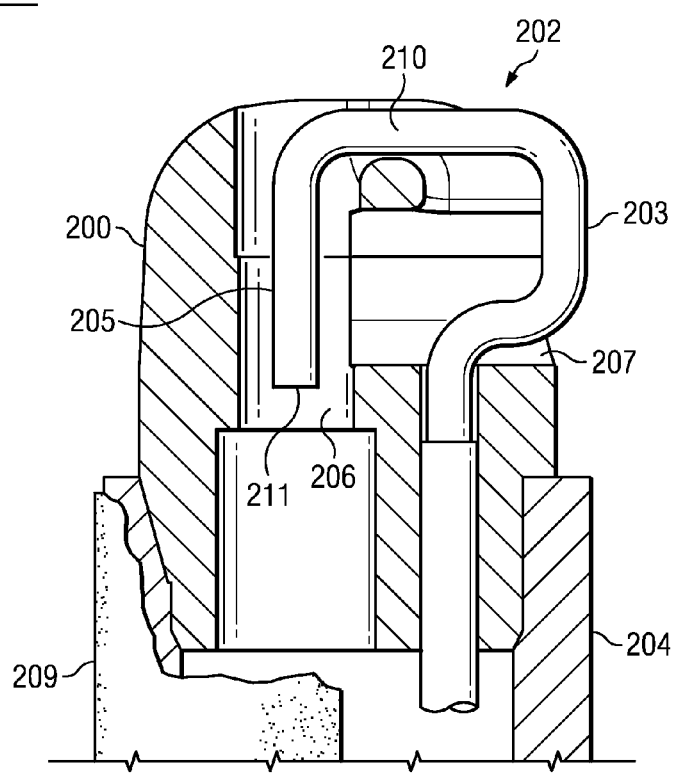
FIG. 3 shows a cross-sectional view of a wand distal end in accordance with at least some embodiments.

In yet still further embodiments, aspiration is provided at the distal end 108 of the wand 102. FIGS. 2 and 3 illustrate aspiration aperture 207 (i.e., suction port 207) at the distal end 108 of the device and disposed through the non-conductive spacer 200. Suction aperture 207 is disposed at distal end 108 and in certain embodiments preferably only located on one side of spacer 200 and disposed through spacer 200 on the same side of shaft 106 as the exposed surface 203 of active electrode 202 and discharge aperture 208. More particularly, and as stated above, suction port 207 is disposed adjacent to and behind exposed surface 203 such that exposed surface 203 bridges or traverses a portion of suction port 207. Suction port 207 provides a path to aspirate the area near the distal end 108, so as to remove excess fluids, ablative by-products, and remnants of ablation created by exposed surface 203 of active electrode 202. The location of suction port 207 further provides for ample wetting of the active and return electrodes, with the saline flowing out from discharge aperture 208 and then being pulled toward active electrode 202 by the fluid flow induced from suction port 207. Applicants have found it is particularly beneficial to provide broader wetting of the exposed surface of return electrode 204, enabling more uniform plasma formation particularly on the exposed surface 203 of active electrode 202.

Referring now to FIG. 3, a cross-section of the distal tip of the wand in accordance with certain embodiments is shown. In particular, digester electrode or digester surface 205 of active electrode 202 is shown. Digester surface 205 is shown disposed within a portion of spacer 200 and located substantially within the aspiration fluid path. In particular, digester surface 205 is disposed coaxially within suction lumen 206, wherein suction lumen 206 is fluidly connected to suction port 207, and where digester surface 205 is recessed away from the opening of suction port 207. In certain embodiments, digester surface 205 is a discrete section of the loop of wire that forms active electrode 202, and digester surface 205 is thereby electrically connected to active electrode 202. Active electrode 202 may be formed in a shape resembling a hook, where exposed surface 203 forms one portion of the hook and digester surface 205 forms the opposite side of the hook, with a contiguous piece of active electrode 202 (secondary surface 210) spanning transversely to the long axis of distal end 108 and routed within a recessed portion of spacer 200. Digester surface 205 is preferably arranged parallel to and co-planar with exposed surface 203 of active electrode 202. Digester surface 205 may preferably include at least one asperity, such as a sharp edge or point, for example surface end 211, where a higher charge density will form, so that when a high frequency voltage is applied between the active electrode and return electrode, a plasma may readily initiate in the presence of an electrically conductive fluid, at this asperity, so as to further morcellate any tissue or ablation by-products that are travelling through the suction lumen 206. Fluids, ablative by-products, and tissue remnants produced by the initial tissue treatment initiated by exposed surface 203 are aspirated away from the tissue treatment site via suction port 207 and into suction lumen 206 such that the ablative by-products are exposed to the electrically-induced effects of digester electrode 205 and thereby further reduced for uninterrupted aspiration. By disposing digester surface 205 within the aspiration fluid flow path, additional ablation and breakdown of the initial ablative by-products is produced in order to minimize clogging of suction lumen 206. Suction lumen 206 is approximately perpendicular to suction port 207 and may be coaxial with the distal end long axis. A diameter of suction lumen 206 may preferably be less than a diameter of the suction port 207, so as fit within the confines of the smaller wand shaft diameter, as described earlier.

As shown for example in FIGS. 2 and 3, return electrode 204 is not directly connected to active electrode 202. To complete a current path so that active electrode 202 is electrically connected to return electrode 204 in the presence of a target tissue, electrically conducting liquid (e.g., isotonic saline) is caused to flow along liquid paths emanating from discharge aperture 208 toward and within suction port 207 and suction 206, and contacting both return electrode 204 and active electrode 202. When a voltage difference is applied between active electrode 202 and return electrode 204, high electric field intensities will be generated at active electrode 202, and particularly adjacent to exposed surface 203 and digester surface 205 of active electrode 202. As current flows from active electrode 202 to the return electrode 204 in the presence of electrically conductive fluid, the high electric field intensities cause ablation of target tissue adjacent exposed surface 203 of active electrode 202. Further ablation and breakdown of aspirated by-products from the initial ablation of the target tissue occurs adjacent digester surface 205 of active electrode 202 in order to prevent clogging of the aspiration features of the device.

Figure 4:
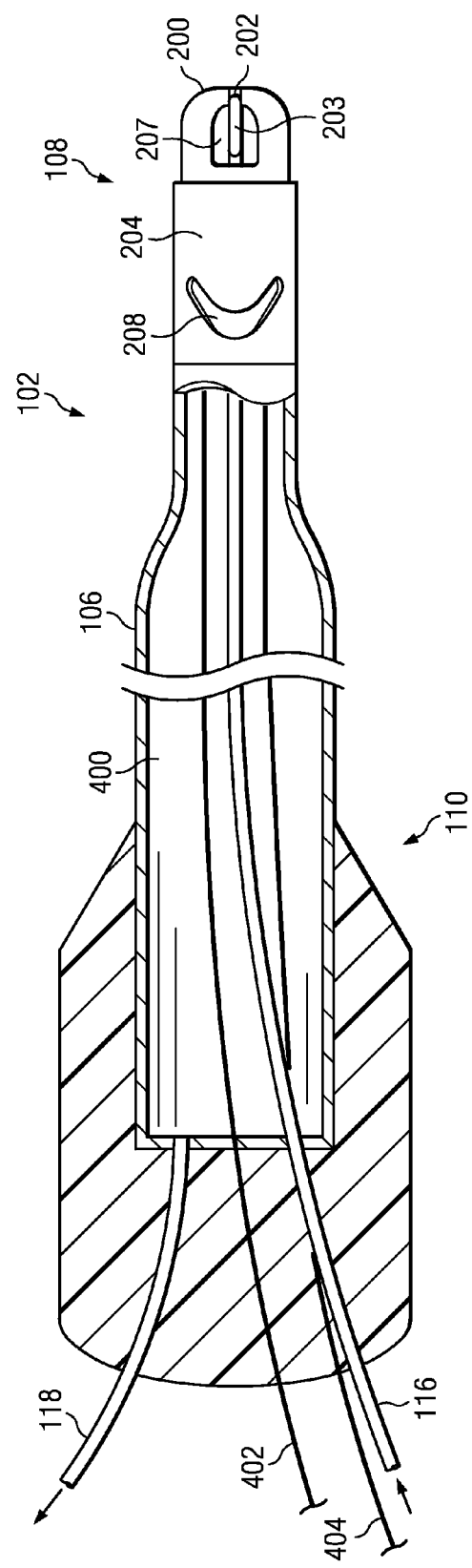
FIG. 4 shows a cross-sectional view of a wand in accordance with at least some embodiments.

FIG. 4 shows a cross-sectional elevation view of a wand 102 in accordance with at least some embodiments. In particular, FIG. 4 shows the handle or proximal end 110 coupled to the elongate shaft 106. As illustrated, the elongate shaft 106 telescopes within the handle, but other mechanisms to couple the elongate shaft to the handle may be equivalently used. The elongate shaft 106 defines internal conduit 400 that serves several purposes. For example, in the embodiments illustrated by FIG. 4 the electrical leads 402 and 404 extend through the internal conduit 400 to electrically couple to the active electrode 202 and return electrode 204, respectively. Likewise, the flexible tubular member 116 extends through the internal conduit 400 to fluidly couple to discharge aperture 208.

The internal conduit 400 also serves as the aspiration route. In particular, FIG. 4 illustrates suction port 207. In the embodiments illustrated the flexible tubular member 118, through which aspiration is performed, couples through the handle and then fluidly couples to the internal conduit 400. Thus, the suction provided through flexible tubular member 118 provides aspiration via suction lumen 206 at the suction port 207. The fluids that are drawn into the internal fluid conduit 400 may abut the portion of the flexible tubular member 116 that resides within the internal conduit as the fluids are drawn along the conduit; however, the flexible tubular member 116 is sealed, and thus the aspirated fluids do not mix with the fluid (e.g., saline) being pumped through the flexible tubular member 116. Likewise, the fluids that are drawn into the internal fluid conduit 400 may abut portions of the electrical leads 402 and 404 within the internal fluid conduit 400 as the fluids are drawn along the conduit. However, the electrical leads are insulated with an insulating material that electrically and fluidly isolates the leads from any substance within the internal fluid conduit 400. Thus, the internal fluid conduit serves, in the embodiments shown, two purposes—one to be the pathway through which the flexible tubular member 116 and electrical leads traverse to reach the distal end 108, and also as the conduit through which aspiration takes place. In other embodiments, the flexible tubular member 118 may extend partially or fully through the elongate shaft 106, and thus more directly couple to the aspiration aperture.

Figure 5:
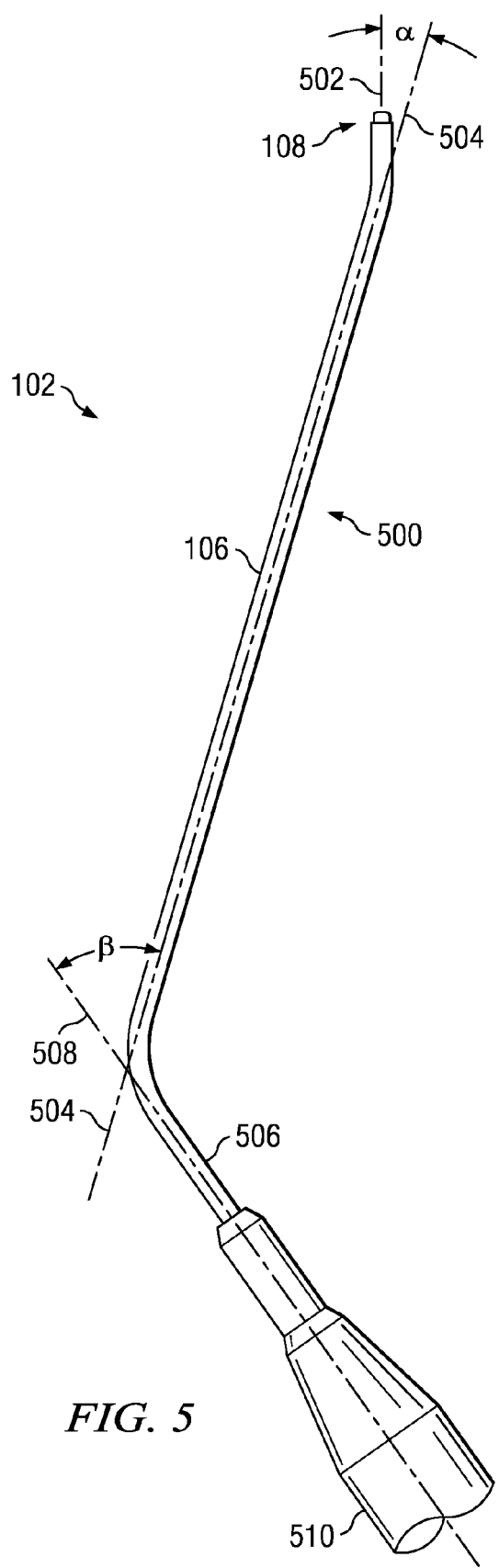
FIG. 5 shows an overhead view of a wand in accordance with at least some embodiments.

The offsets of the elongate shaft 106 are not visible in FIG. 4 because of the particular view; however, FIG. 5 shows illustrative offsets. FIG. 5 shows an overhead view of the wand 102 in an orientation where the offsets in the elongate shaft 106 are visible. The illustrative wand 102 is designed and constructed for use in procedures where other equipment (e.g., an arthroscopic camera or surgical microscope) may be present and where those other devices prevent use of straight elongate shaft. In particular, the distal end 108 defines wand tip axis 502, and the elongate shaft 106 also defines a medial portion 500 which has an axis 504 (hereafter, the medial axis 504). In the particular embodiments illustrated the angle $\alpha$ between the medial axis 504 and the wand tip axis 502 is non-zero, and in some embodiments the acute angle $\alpha$ between the medial axis 504 and the wand tip axis 502 is 16 degrees, but greater or lesser angles may be equivalently used.

Likewise, the elongate shaft 106 of FIG. 5 defines a proximal portion 506 with an axis 508 (hereafter, the proximal axis 508). In the particular embodiment illustrated the angle $\beta$ between the proximal axis 508 and the medial axis 504 is non-zero, and in some embodiments the acute angle $\beta$ between the proximal axis 508 and the medial axis 504 is 55 degrees, but greater or lesser angles may be equivalently used.

Figure 6A:
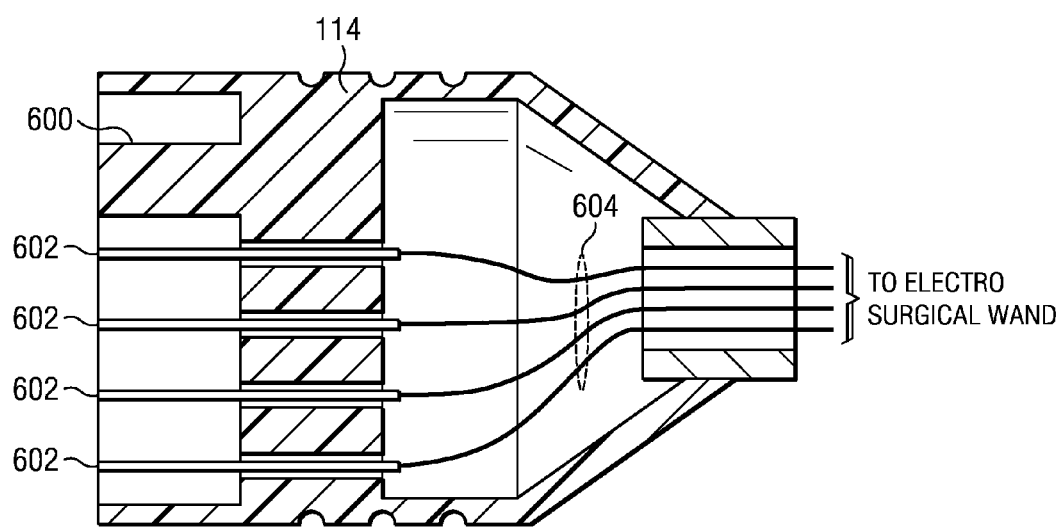
FIG. 6A shows a cross-sectional view of a wand connector in accordance with at least some embodiments.
Figure 6B:
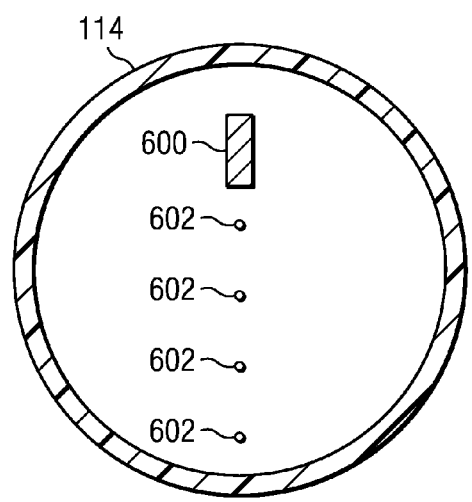
FIG. 6B shows an elevational end-view of a wand connector in accordance with at least some embodiments.

As illustrated in FIG. 1, flexible multi-conductor cable 112 (and more particularly its constituent electrical leads 402, 404 and possibly others) couple to the wand connector 114. Wand connector 114 couples the controller 104, and more particularly the controller connector 120. FIG. 6 shows both a cross-sectional view (right) and an end elevation view (left) of wand connector 114 in accordance with at least some embodiments. In particular, wand connector 114 comprises a tab 600. Tab 600 works in conjunction with a slot on controller connector 120 (shown in FIG. 7) to ensure that the wand connector 114 and controller connector 120 only couple in one relative orientation. The illustrative wand connector 114 further comprises a plurality of electrical pins 602 protruding from wand connector 114. In many cases, the electrical pins 602 are coupled one each to an electrical lead of electrical leads 604 (two of which may be leads 402 and 404 of FIG. 4). Stated otherwise, in particular embodiments each electrical pin 602 couples to a single electrical lead, and thus each illustrative electrical pin 602 couples to a single electrode of the wand 102. In other cases, a single electrical pin 602 couples to multiple electrodes on the electrosurgical wand 102. While FIG. 6 shows four illustrative electrical pins, in some embodiments as few as two electrical pins, and as many as 26 electrical pins, may be present in the wand connector 114.

Figure 7A:
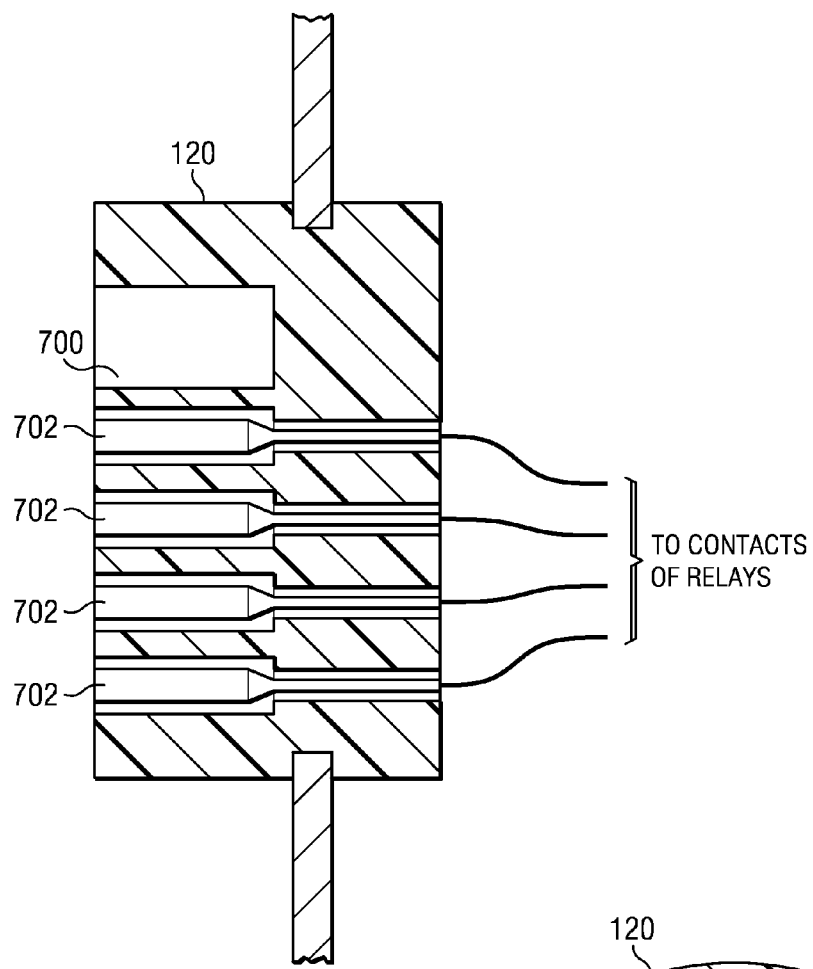
FIG. 7A shows a cross-sectional view of a controller connector in accordance with at least some embodiments.
Figure 7B:
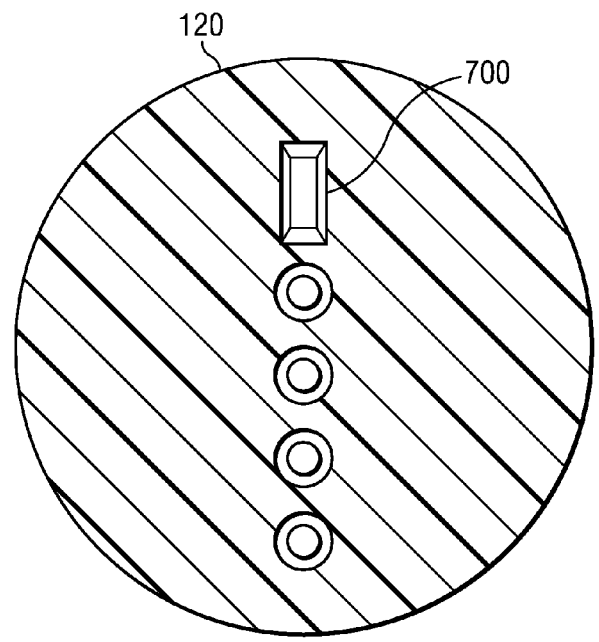
FIG. 7B shows both an elevational end-view of a controller connector in accordance with at least some embodiments.

FIG. 7 shows both a cross-sectional view (right) and an end elevation view (left) of controller connector 120 in accordance with at least some embodiments. In particular, controller connector 120 comprises a slot 700. Slot 700 works in conjunction with a tab 600 on wand connector 114 (shown in FIG. 5) to ensure that the wand connector 114 and controller connector 120 only couple in one orientation. The illustrative controller connector 120 further comprises a plurality of electrical pins 702 residing within respective holes of controller connector 120. The electrical pins 702 are coupled to terminals of a voltage generator within the controller 104 (discussed more thoroughly below). When wand connector 114 and controller connector 120 are coupled, each electrical pin 702 couples to a single electrical pin 602. While FIG. 7 shows only four illustrative electrical pins, in some embodiments as few as two electrical pins and as many as 26 electrical pins may be present in the wand connector 120.

While illustrative wand connector 114 is shown to have the tab 600 and male electrical pins 602, and controller connector 120 is shown to have the slot 700 and female electrical pins 702, in alternative embodiments the wand connector has the female electrical pins and slot, and the controller connector 120 has the tab and male electrical pins, or other combination. In other embodiments, the arrangement of the pins within the connectors may enable only a single orientation for connection of the connectors, and thus the tab and slot arrangement may be omitted. In yet still other embodiments, other mechanical arrangements to ensure the wand connector and controller connector couple in only one orientation may be equivalently used. In the case of a wand with only two electrodes, and which electrodes may be either active or return electrodes as the physical situation dictates, there may be no need to ensure the connectors couple in a particular orientation.

Figure 8:
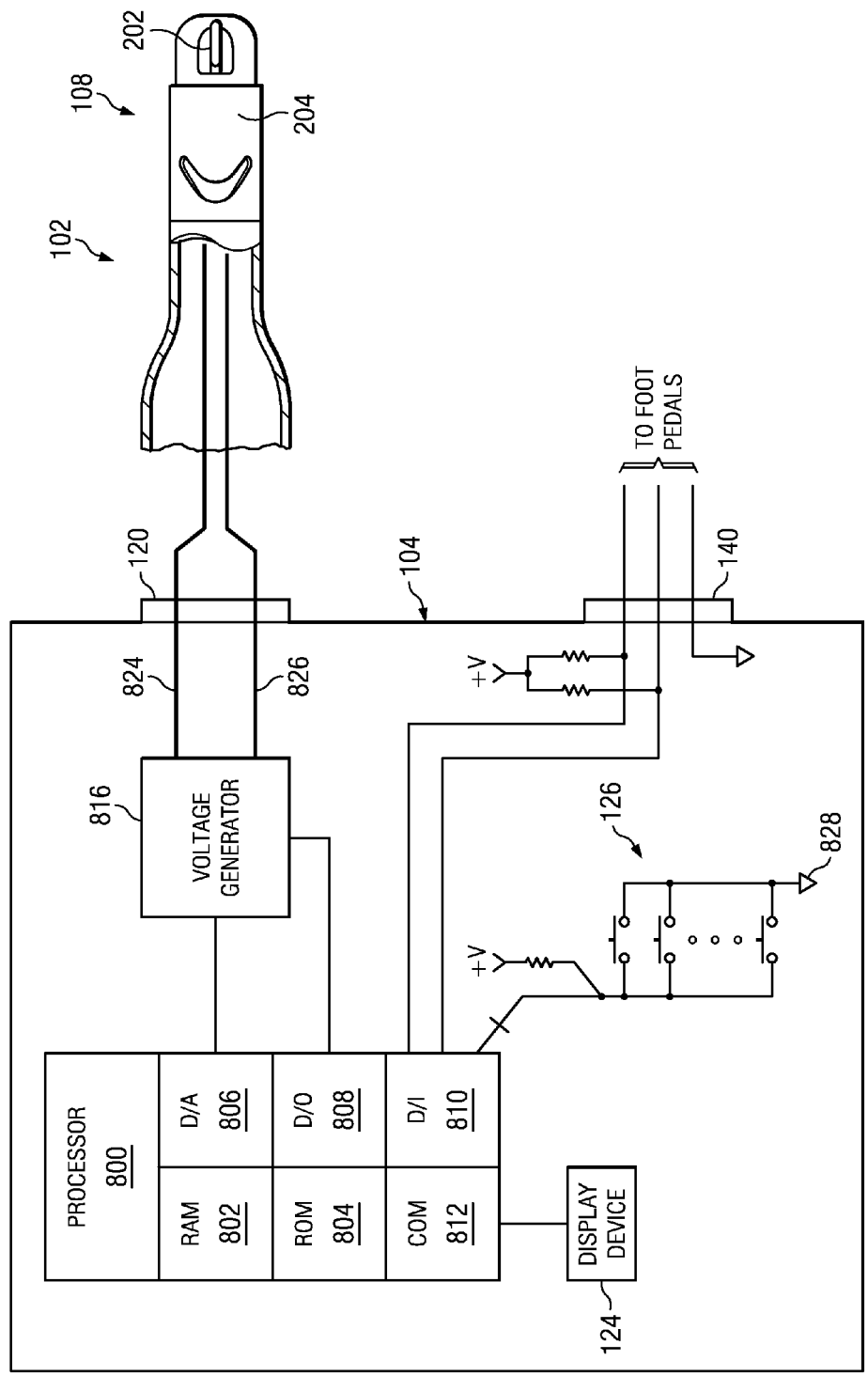
FIG. 8 shows an electrical block diagram of an electrosurgical controller in accordance with at least some embodiments.

FIG. 8 illustrates a controller 104 in accordance with at least some embodiments. In particular, the controller 104 comprises a processor 800. The processor 800 may be a microcontroller, and therefore the microcontroller may be integral with random access memory (RAM) 802, read-only memory (RAM) 804, digital-to-analog converter (D/A) 806, digital outputs (D/O) 808 and digital inputs (D/I) 810. The processor 800 may further provide one or more externally available peripheral busses, such as a serial bus (e.g., I2C), parallel bus, or other bus and corresponding communication mode. The processor 800 may further be integral with a communication logic 812 to enable the processor 800 to communicate with external devices, as well as internal devices, such as display deice 124. Although in some embodiments the controller 104 may implement a microcontroller, in yet other embodiments the processor 800 may be implemented as a standalone central processing unit in combination with individual RAM, ROM, communication, D/A, D/O and D/I devices, as well as communication port hardware for communication to peripheral components.

ROM 804 stores instructions executable by the processor 800. In particular, the ROM 804 may comprise a software program that implements the various embodiments of periodically reducing voltage generator output to change position of the plasma relative to the electrodes of the wand (discussed more below), as well as interfacing with the user by way of the display device 124 and/or the foot pedal assembly 130 (FIG. 1). The RAM 802 may be the working memory for the processor 800, where data may be temporarily stored and from which instructions may be executed. Processor 800 couples to other devices within the controller 104 by way of the D/A converter 806 (e.g., the voltage generator 816), digital outputs 808 (e.g., the voltage generator 816), digital inputs 810 (i.e., push button switches 126, and the foot pedal assembly 130 (FIG. 1)), and other peripheral devices.

Voltage generator 816 generates selectable alternating current (AC) voltages that are applied to the electrodes of the wand 102. In the various embodiments, the voltage generator defines two terminals 824 and 826. In accordance with the various embodiments, the voltage generator generates an alternating current (AC) voltage across the terminals 824 and 826. In at least some embodiments the voltage generator 816 is electrically "floated" from the balance of the supply power in the controller 104, and thus the voltage on terminals 824, 826, when measured with respect to the earth ground or common (e.g., common 828) within the controller 104, may or may not show a voltage difference even when the voltage generator 816 is active.

The voltage generated and applied between the active terminal 824 and return terminal 826 by the voltage generator 816 is a RF signal that, in some embodiments, has a frequency of between about 5 kilo-Hertz (kHz) and 20 Mega-Hertz (MHz), in some cases being between about 30 kHz and 2.5 MHz, often between about 100 kHz and 200 kHz. In applications associated with otolaryngology—head and neck procedures, a frequency of about 100 kHz appears most effective. The RMS (root mean square) voltage generated by the voltage generator 816 may be in the range from about 5 Volts (V) to 1000 V, preferably being in the range from about 10 V to 500 V, often between about 100 V to 350 V depending on the active electrode size and the operating frequency. The peak-to-peak voltage generated by the voltage generator 816 for ablation or cutting in some embodiments is a square wave form in the range of 10 V to 2000 V and in some cases in the range of 100 V to 1800 V and in other cases in the range of about 28 V to 1200 V, often in the range of about 100 V to 320 V peak-to-peak (again, depending on the electrode size and the operating frequency).

Still referring to the voltage generator 816, the voltage generator 816 delivers average power levels ranging from several milliwatts to hundreds of watts per electrode, depending on the voltage applied for the target tissue being treated, and/or the maximum allowed temperature selected for the wand 102. The voltage generator 816 is configured to enable a user to select the voltage level according to the specific requirements of a particular procedure. A description of one suitable voltage generator 816 can be found in commonly assigned U.S. Pat. Nos. 6,142,992 and 6,235,020, the complete disclosure of both patents are incorporated herein by reference for all purposes.

In some embodiments, the various operational modes of the voltage generator 816 may be controlled by way of digital-to-analog converter 806. That is, for example, the processor 800 may control the output voltage by providing a variable voltage to the voltage generator 816, where the voltage provided is proportional to the voltage generated by the voltage generator 816. In other embodiments, the processor 800 may communicate with the voltage generator by way of one or more digital output signals from the digital output 808 device, or by way of packet based communications using the communication device 812 (connection not specifically shown so as not to unduly complicate FIG. 8).

FIG. 8 also shows a simplified side view of the distal end 108 of the wand 102. As shown, illustrative active electrode 202 of the wand 102 electrically couples to terminal 824 of the voltage generator 816 by way of the connector 120, and return electrode 204 electrically couples to terminal 826 of the voltage generator 816.

Figure 9:
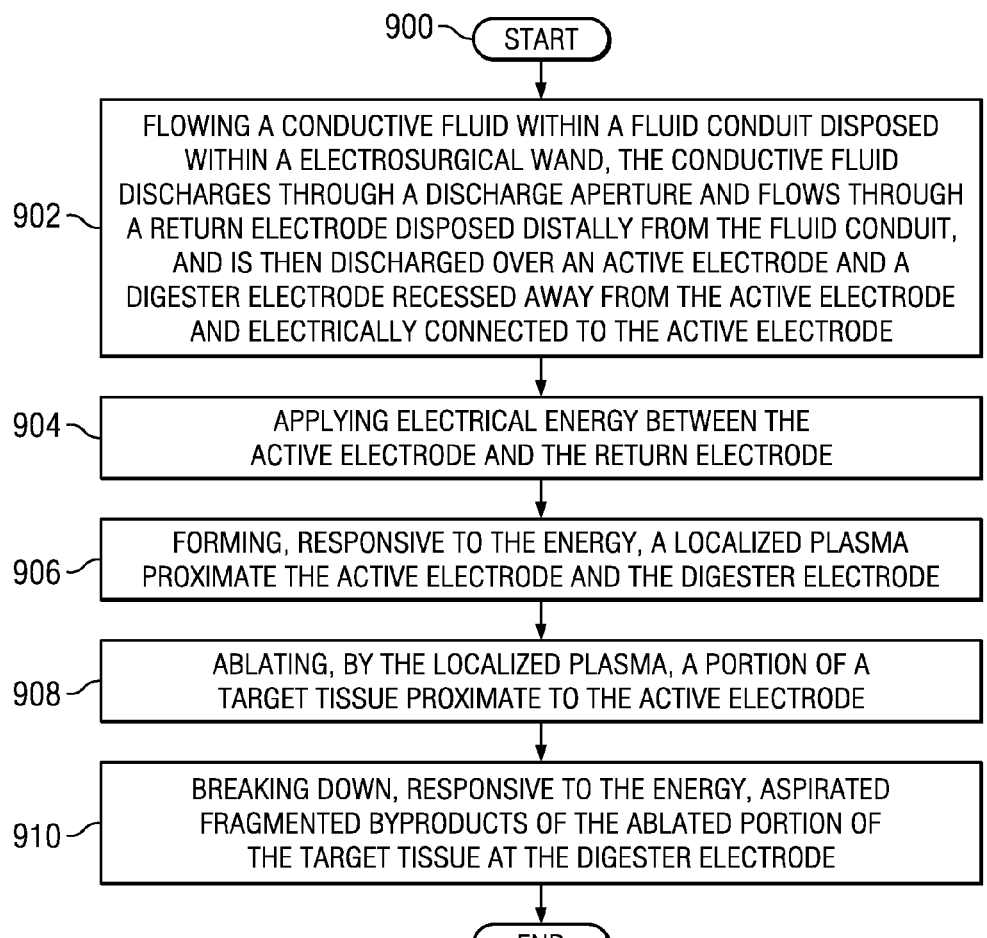
FIG. 9 shows a method in accordance with at least some embodiments.

FIG. 9 shows a method in accordance with at least some embodiments. In particular, the method starts (block 900) and proceeds to: flowing a conductive fluid within a fluid conduit disposed within a electrosurgical wand, the conductive fluid discharges through a discharge aperture and flows through a return electrode disposed distally from the fluid conduit, and is then discharged over an active electrode and a digester electrode recessed away from the active electrode and electrically connected to the active electrode (block 902); applying electrical energy between the active electrode and the return electrode (block 904); forming, responsive to the energy, a localized plasma proximate the active electrode and the digester electrode (block 906); ablating, by the localized plasma, a portion of a target tissue proximate to the active electrode (block 908); and breaking down, responsive to the energy, aspirated fragmented by-products of the ablated portion of the target tissue proximate to the digester electrode (block 910). And thereafter the method ends (block 912).

The above discussion is meant to be illustrative of the principles and various embodiments of the present invention. Numerous variations and modifications possible. For example, while in some cases electrodes were designated as upper electrodes and lower electrodes, such a designation was for purposes of discussion, and shall not be read to require any relationship to gravity during surgical procedures. It is intended that the following claims be interpreted to embrace all such variations and modifications.

While preferred embodiments of this disclosure have been shown and described, modifications thereof can be made by one skilled in the art without departing from the scope or teaching herein. The embodiments described herein are exemplary only and are not limiting. Because many varying and different embodiments may be made within the scope of the present inventive concept, including equivalent structures, materials, or methods hereafter thought of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical wand for electrosurgically treating a target tissue comprising:
   an elongate shaft having a proximal handle end and a distal end and a non-conductive spacer coupled to the shaft distal end, wherein the spacer comprises a suction aperture disposed on a lateral side of the spacer and fluidly connected with a suction lumen disposed within the spacer; and
   a loop of wire defining;
      an active electrode exposed surface portion bridging the suction aperture; and
      a digester electrode surface portion facing the suction aperture, and disposed within the suction lumen.

2. The electrosurgical wand of claim 1, wherein the loop of wire further defines an active electrode recessed surface portion, electrically connected between the active electrode exposed surface and the digester electrode surface and wherein a distal outer surface of the spacer comprises an elongate recess, configured to nest the active electrode recessed surface.

3. The electrosurgical wand of claim 1, further comprising a semi annular return electrode disposed proximally to the spacer, wherein the return electrode defines a portion of the shaft distal end and is disposed on the side of the shaft corresponding to the active electrode exposed surface portion.

4. The electrosurgical wand of claim 3, further comprising an irrigation aperture disposed through the return electrode, fluidly connected with a fluid conduit, operable to supply an electrically conductive fluid to the distal end.

5. The electrosurgical wand of claim 1, wherein the suction aperture is approximately perpendicular to the suction lumen.

6. The electrosurgical wand of claim 1, wherein the active electrode surface portion and the digester electrode surface portion both have elongate surfaces that are substantially parallel to each other.

7. The electrosurgical wand of claim 1, wherein the digester electrode surface portion defines a long axis that is substantially parallel with a long axis of the suction lumen.

8. The electrosurgical wand of claim 1, wherein the digester electrode surface portion defines an end portion of the loop of wire, a terminus of the end portion defining an asperity, configured to readily initiate plasma adjacent said asperity and thereby the digester electrode surface portion, in the presence of a high frequency voltage and electrically conductive fluids.

9. The electrosurgical wand of claim 1, wherein the digester electrode surface portion has a long axis that is coaxial with a suction lumen long axis.

10. The electrosurgical wand of claim 1 wherein the suction aperture has a first diameter and the suction lumen has a second diameter that is smaller than the first diameter.

11. The electrosurgical wand of claim 10 wherein the digester electrode surface defines an elongate surface that is disposed along the second diameter portion of the suction lumen and adjacent an intersection between the first diameter and the second diameter.

12. The electrosurgical wand of claim 1 wherein the loop of wire defines a hook shape.

13. An electrosurgical wand for electrosurgically treating a target tissue comprising:
   an elongate shaft having a proximal handle end and a distal end and a non-conductive spacer coupled to the shaft distal end, wherein the spacer comprises a suction aperture disposed on a lateral side of the spacer, the suction aperture defining an open end of a suction channel having a length extending towards and fluidly connected at a medial end of the suction channel with a suction lumen disposed within the spacer;
   a length of wire determining at least two different surface portions, including
      an active electrode exposed surface covering at least a portion of the suction aperture; and
      a digester electrode elongate surface portion disposed directly opposite the suction aperture and within the suction lumen.

14. The electrosurgical wand of claim 13, wherein the length of wire further comprises an active electrode recessed surface portion, recessed away from a distal surface of the spacer.

15. The electrosurgical wand of claim 14 wherein the recessed surface portion lies along an elongate channel disposed along the distal surface of the spacer, the elongate channel having a depth configured so that the active electrode recessed surface may selectively treat a target tissue.

16. The electrosurgical wand of claim 13, wherein the length of wire further defines an second active electrode portion extending from the active electrode exposed surface portion and into and along a portion of the suction channel length, configured so that a portion of target tissue may be treated as the target tissue is aspirated along the suction channel.

17. The electrosurgical wand of claim 13, wherein the suction channel length defines a longitudinal axis that is approximately perpendicular to a longitudinal axis of the suction lumen.

18. The electrosurgical wand of claim 13, wherein the digester electrode elongate surface portion is substantially parallel with a long axis of the elongate shaft.

19. The electrosurgical wand of claim 13 wherein the suction aperture has a first diameter and the suction lumen has a second diameter that is smaller than the first diameter and wherein the first digester electrode surface portion is disposed within the suction lumen and adjacent where the first diameter and the second diameter intersect.

* * * * *